(12) United States Patent
Morgan et al.

(10) Patent No.: US 9,913,796 B2
(45) Date of Patent: Mar. 13, 2018

(54) ORAL CARE COMPOSITION CONTAINING PUMICE AND CALCIUM CARBONATE

(71) Applicant: Colgate-Palmolive Company, Piscataway, NJ (US)

(72) Inventors: Andre Morgan, Robbinsville, NJ (US); Vyoma Patel, Parsippany, NJ (US); Marilou Joziak, South River, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/781,907

(22) PCT Filed: May 13, 2013

(86) PCT No.: PCT/US2013/040694
§ 371 (c)(1),
(2) Date: Oct. 1, 2015

(87) PCT Pub. No.: WO2014/185884
PCT Pub. Date: Nov. 20, 2014

(65) Prior Publication Data
US 2016/0030330 A1 Feb. 4, 2016

(51) Int. Cl.
| | | |
|---|---|---|
| *A61K 8/96* | (2006.01) | |
| *A61K 8/44* | (2006.01) | |
| *A61K 8/02* | (2006.01) | |
| *A61K 8/19* | (2006.01) | |
| *A61K 8/21* | (2006.01) | |
| *A61Q 11/00* | (2006.01) | |

(52) U.S. Cl.
CPC ............ *A61K 8/965* (2013.01); *A61K 8/0204* (2013.01); *A61K 8/0241* (2013.01); *A61K 8/19* (2013.01); *A61K 8/21* (2013.01); *A61K 8/44* (2013.01); *A61Q 11/00* (2013.01); *A61K 2800/28* (2013.01); *A61K 2800/41* (2013.01); *A61K 2800/412* (2013.01); *A61K 2800/592* (2013.01)

(58) Field of Classification Search
CPC ...... A61K 8/0204; A61K 8/0241; A61K 8/19; A61K 8/21; A61K 8/44; A61K 8/965; A61K 2800/28; A61K 2800/41; A61K 2800/412; A61K 2800/592; A61Q 11/00
See application file for complete search history.

(56) References Cited

U.S. PATENT DOCUMENTS

| | | | |
|---|---|---|---|
| 2,623,003 A | 12/1952 | Friedlob et al. | |
| 3,257,282 A | 6/1966 | Muhler | |
| 3,330,732 A | 7/1967 | Muhler | |
| 3,378,445 A | 4/1968 | Muhler | |
| 3,452,382 A | 7/1969 | Kazdan | |
| 4,708,864 A * | 11/1987 | Maurer | A61K 8/365 424/49 |
| 6,660,250 B1 * | 12/2003 | Higgins | A61C 17/00 424/49 |
| 8,221,723 B2 | 7/2012 | Deckner et al. | |
| 8,221,726 B2 | 7/2012 | Deckner et al. | |
| 8,226,932 B2 | 7/2012 | Haught et al. | |
| 8,293,216 B2 | 10/2012 | Deckner et al. | |
| 2002/0064504 A1 * | 5/2002 | Kleinberg | A61K 8/19 424/49 |
| 2003/0072721 A1 * | 4/2003 | Riley | A61K 8/19 424/49 |
| 2012/0067748 A1 | 3/2012 | Jung et al. | |

FOREIGN PATENT DOCUMENTS

| | | |
|---|---|---|
| GB | 10940 | 6/1913 |
| GB | 413385 | 7/1934 |
| GB | 550345 | 1/1943 |
| WO | WO 00/10520 | 3/2000 |
| WO | WO 2012/057739 | 5/2012 |

OTHER PUBLICATIONS

International Search Report & Written Opinion for international Application No. PCT/US2013/040694 dated Mar. 17, 2014.

* cited by examiner

*Primary Examiner* — Michael B. Pallay

(57) ABSTRACT

Disclosed are oral care compositions comprising an abrasive system, wherein the abrasive system comprises (a) a first particulate abrasive comprising at least 20 wt % pumice, based on the weight of the oral care composition, having an average particle size of from 20 to 300 microns; and (b) a second particulate abrasive comprising calcium carbonate having an average particle size of from 2 to 13 microns. There is also disclosed a method of cleaning teeth comprising applying the oral care composition to a tooth surface, the oral care composition being applied as a paste disposed in a prophy cup.

24 Claims, No Drawings

ORAL CARE COMPOSITION CONTAINING PUMICE AND CALCIUM CARBONATE

The present invention relates to an oral care composition which exhibits enhanced cleaning benefits, suitable for providing a dental prophylaxis, while maintaining low abrasivity.

Dental prophylaxis is most likely the most common procedure performed in the dental office. The purpose of a dental prophylaxis or prophy is to clean teeth by removing plaque, calculus, and dental stains in order to ultimately help prevent cavities and periodontal disease; and to polish teeth in order to smooth the surface, providing gloss and luster. The dental prophy procedure involves using a paste along with a prophy angle equipped with a prophy cup.

Paste used during the prophy procedure primarily consists of abrasives, binders, humectants, flavors, and preservatives. The abrasive system plays a key role in determining how effective the paste will be in cleaning and polishing the teeth, while not negatively impacting the tooth surface. The type of abrasives used (e.g. pumice, silica, calcium carbonate, aluminum oxide), the physical properties of the abrasive (i.e. particle size and hardness), and the overall concentration of the abrasives in the formula are critical parameters one needs to consider in order to formulate an equally effective and orally safe prophy paste.

There is a need in the art for an oral care composition formulated as a prophy paste containing an abrasive system that offers improved cleaning attributes, while maintaining low abrasivity.

Dentin is a portion of the tooth internal to the enamel and cementum that has a radially striated appearance owing to a large number of fine canals or tubules known as the dentinal tubules. Tubules run from the pulp cavity to the periphery of the dentin and are generally about two microns in diameter at their base and somewhat narrower at their periphery. Tubules are not usually exposed to the environment in the oral cavity, as they are usually covered by enamel or cementum. The cementum in turn is often covered by the gums.

It is commonly understood that partially or fully exposed tubules can lead to tooth sensitivity, an irritating and painful condition. In this theory, recession of the gum line exposes cementum to erosion. The eroded cementum in turn exposes the hollow dentinal tubules. The exposed tubules cause nerves within the tooth to be affected excessively by external oral stimuli because material and energy transfer between the exterior and interior of the tooth is accelerated through the tubules. Common environmental stimuli, such as heat, cold, chemicals and physical and mechanical pressure or stimuli, such as brushing, are able to irritate the nerve through the open dentin tubules and thereby create pain. The pain of sensitive teeth appears to result from these stimuli, which apparently cause fluid movements in the dentinal tubules that activate pulpal nerve endings.

Conventionally, two approaches have been taken to treat or ameliorate tooth sensitivity. Under one approach, the chemical environment proximal to the nerve is altered by application of various agents, such that the nerve is not stimulated, or not stimulated as greatly. Known agents useful in this chemical approach, including potassium salts (such as potassium nitrate, potassium bicarbonate, potassium chloride) and strontium, zinc salts, and chloride salts.

The second approach involves the mechanical shield of the nerve by, e.g., blocking of the dentinal tubules wholly or partially with "tubule blocking agents." Agents that have been disclosed in the prior art include, e.g., cationic alumina, clays, water-soluble or water-swellable polyelectrolytes, oxalates, amorphous calcium phosphate, hydroxyapatite, maleic acid copolymers and polyethylene particles.

WO-A1-2012/057739 in the name of the present Applicant discloses the provision of an oral care composition comprising arginine and calcium carbonate that reduces and/or eliminates the perception of tooth sensitivity.

However, even though such an oral care composition provides clinical hypersensitivity relief, there is nevertheless still a need in the art for an oral care composition, which, upon use, provides enhanced prevention or reduction of tooth sensitivity and is formulated for application to the oral cavity in a convenient form for providing substantially immediate relief over a period of time as well as enhanced cleaning and low abrasivity to enable the composition to be used effectively as a prophy paste.

There is also a need in the art for an oral care composition formulated for dental prophylaxis as a prophy paste and hypersensitivity treatment containing an abrasive system that offers improved cleaning attributes, while maintaining low abrasivity.

BRIEF SUMMARY OF THE INVENTION

The aim of this invention is to provide an oral care composition, which, upon use, provides enhanced cleaning attributes, while maintaining low abrasivity, and which can also optionally assist in the prevention or reduction of tooth sensitivity, in particular in a hypersensitivity treatment.

The invention accordingly provides an oral care composition comprising an abrasive system, wherein the abrasive system comprises: (a) a first particulate abrasive comprising at least 20 wt % pumice, based on the weight of the oral care composition, having an average particle size of from 20 to 300 microns; and (b) a second particulate abrasive comprising calcium carbonate having an average particle size of from 2 to 13 microns. The term average particle size as used herein refers to the particle size distribution D50.

Optionally, the first particulate abrasive comprises from 20 to 60 wt % pumice, based on the weight of the oral care composition. Further optionally, the first particulate abrasive comprises from 30 to 50 wt % pumice, based on the weight of the oral care composition.

Optionally, the second particulate abrasive comprises calcium carbonate in an amount of from 5 to 40 wt %, based on the weight of the oral care composition. Further optionally, the second particulate abrasive comprises calcium carbonate in an amount of from 15 to 30 wt %, based on the weight of the oral care composition.

Optionally, the weight ratio between the first particulate abrasive and the second particulate abrasive is within a range from the group consisting of 0.6-5.0:1, 0.7-4.0:1, and 1.0-3.5:1.

Optionally, the calcium carbonate has an average particle size of from 4 to 10 microns.

Optionally, the calcium carbonate comprises of a first calcium carbonate with an average particle size of from 4 to 5 microns and a second calcium carbonate with an average particle size of from 9 to 10 microns.

Optionally, the weight ratio of the first calcium carbonate with an average particle size of from 4 to 5 microns to the second calcium carbonate with an average particle size of from 9 to 10 microns is selected from group consisting of 1.0-1.2:1 and 1.05-1.15:1.

Optionally, the calcium carbonate comprises natural calcium carbonate particles.

Optionally, at least a portion of the particles of calcium carbonate comprise natural calcium carbonate have an average particle size of no greater than a dentin tubule of a mammalian tooth.

Optionally, the oral care composition further comprises a basic amino acid in free or salt form in an amount effective for treating dental hypersensitivity. Further optionally, the basic amino acid in free or salt form comprises arginine bicarbonate.

Optionally, the basic amino acid in free or salt form is present in an amount of from 5 to 15 wt % based on the weight of the oral care composition. Further optionally, the basic amino acid in free or salt form is present in an amount of from 7 to 12 wt % based on the weight of the oral care composition.

Optionally, the oral care composition further comprises an orally acceptable vehicle. Further optionally, the orally acceptable vehicle comprises glycerin which is present in an amount of from 5 to 20 wt % based on the weight of the oral care composition. Yet further optionally, the glycerin is present in an amount of from 10 to 15 wt % based on the weight of the oral care composition.

Optionally, the oral care composition further comprises a fluoride compound or a source of fluorine ions.

Optionally, the amount and particle size of the first and second particulate abrasives are selected to provide the oral care composition with a pellicle cleaning ratio (PCR) of at least 59, a radioactive dentin abrasion (RDA) of no more than 250, and a ratio of the pellicle cleaning ratio (PCR) to the radioactive dentin abrasion (RDA) of at least 0.6. Further optionally, the amount and particle size of the first and second particulate abrasives are selected to provide the oral care composition with a pellicle cleaning ratio (PCR) of from 70 to 110, a radioactive dentin abrasion (RDA) of from 100 to 140, and a ratio of the pellicle cleaning ratio (PCR) to the radioactive dentin abrasion (RDA) of from 0.6 to 0.8, optionally from 0.64 to 0.8.

Optionally, the composition is formulated into a dentifrice in the form of a paste.

The invention further provides a method of cleaning teeth comprising applying the oral care composition of the invention to a tooth surface, the oral care composition being applied as a paste disposed in a prophy cup.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity, improving/maintaining systemic health, and/or occluding dentin tubules.

Some embodiments of the invention relate to a desensitizing oral care composition comprised of pumice and calcium carbonate abrasives that offer improved cleaning attributes, while maintaining low abrasivity. In some embodiments, the pumice has an average particle size between 20 to 300 microns, or more preferably between 90 to 300 microns. In some embodiments, the calcium carbonate has an average particle size of 2 to 13 microns, or more preferably 2 to 10 microns. In some embodiments, the composition of the abrasive system can consist of 20 to 60 wt % pumice, or more preferably 30 to 50 wt % pumice, in combination with 5 to 40 wt % calcium carbonate, or more preferably 15 to 30 wt % calcium carbonate, each amount being based on the total weight of the oral care composition.

In some embodiments, the oral care composition provides a pellicle cleaning ratio (PCR) of at least about 59, typically 70 or greater. In some embodiments, the oral care composition provides a radioactive dentin abrasion value (RDA) of about 250 or less. In some embodiments, the oral care composition the ratio of PCR to RDA is at least about 0.6 or greater, or more preferably, 0.64 or greater.

In some embodiments, the oral care composition also contains a dentin tubule occluding agent able to provide hypersensivity relief. The preferred dentin tubule occluding agent is an amino acid, for example L-arginine, or a salt thereof, such as the bicarbonate salt, in combination with a sparingly soluble calcium source (i.e. calcium carbonate) proven to reduce tooth sensitivity by blocking dentin tubules.

In some embodiments, other suitable combinations of dentin tubule occluding agents may be employed, which include, but are not limited to, L-arginine or other amino acids, such as lysine or serine, in combination with sparingly soluble metal sources, such as zinc oxide, dicalcium phosphate, tricalcium phosphate. In some embodiments, other dentin tubule occluding agents that provide hypersensitivity relief may include, but are not limited to bioactive glass (5-20 wt %); small particle silica (3-5 microns in size, 5-20 wt %); and strontium salts, such as strontium chloride and strontium acetate (5-15 wt %), all weights being based on the total weight of the composition. Any combination of these various dentin tubule occluding agents may be employed. In addition to dentin tubule occluding agents, in some embodiments the oral care composition may also contain potassium nitrate, also proven to provide hypersensitivity relief.

The present invention is at least partly predicated on the finding by the present inventors that, in an oral care composition comprising abrasives for providing cleaning efficacy so that the composition may be used as a prophylactic prophy paste in a prophy cup, a specific combination of pumice, having a particular average particle size profile, and calcium carbonate, having a particular average particle size profile, can provide enhanced cleaning benefits coupled with low abrasion of the tooth enamel, with the result that a high PCR/RDA ratio between the pellicle cleaning ratio (PCR) and the radioactive dentin abrasion (RDA) can be achieved.

The present invention is further at least partly predicated on the finding by the present inventors that in such an oral care composition which also comprises a basic amino acid in free or salt form and particles of calcium carbonate, for example natural calcium carbonate, for treating or relieving hypersensitivity, the resultant composition can be formulated for use as a prophylactic prophy paste which can be applied to the tooth surface using a prophy cup and additionally provides effective relief against dental hypersensitivity.

DETAILED DESCRIPTION OF THE INVENTION

It should be understood that the detailed description and specific examples, while indicating embodiments of the invention, are intended for purposes of illustration only and are not intended to limit the scope of the invention.

As referred to herein, all compositional percentages are by weight of the total composition, unless otherwise specified.

The invention described herein includes an oral care composition comprising an abrasive system, wherein the abrasive system comprises: (a) a first particulate abrasive comprising at least 20 wt % pumice, based on the weight of the oral care composition, having an average particle size of from 20 to 300 microns; and (b) a second particulate abrasive comprising calcium carbonate having an average particle size of from 2 to 13 microns.

The invention further provides a method of cleaning teeth comprising applying the oral care composition of the invention to a tooth surface, the oral care composition being applied as a paste disposed in a prophy cup.

Abrasive System

The present invention is at least partly based on the finding by the present inventors that a particular mixed abrasive system of pumice and calcium carbonate may have high tooth cleaning efficacy as measured for example by the pellicle cleaning ratio (PCR) radioactive dentin abrasion (RDA), with dentin abrasion as measured for example by radioactive dentin abrasion (RDA), in the composition of the invention which may also comprise a system for relieving dentin hypersensitivity which includes a basic amino acid in free or salt form and particles of calcium carbonate, for example natural calcium carbonate.

Typically, the amount and particle size of the first and second particulate abrasives are selected to provide the oral care composition with a pellicle cleaning ratio (PCR) of at least 59, a radioactive dentin abrasion (RDA) of no more than 250, and a ratio of the pellicle cleaning ratio (PCR) to the radioactive dentin abrasion (RDA) of at least 0.6. More typically, the amount and particle size of the first and second particulate abrasives are selected to provide the oral care composition with a pellicle cleaning ratio (PCR) of from 70 to 110, a radioactive dentin abrasion (RDA) of from 100 to 140, and a ratio of the pellicle cleaning ratio (PCR) to the radioactive dentin abrasion (RDA) of from 0.6 to 0.8, preferably from 0.64 to 0.8.

Typically, the first particulate abrasive comprises from 20 to 60 wt % pumice, based on the weight of the oral care composition, for example from 30 to 50 wt % pumice, based on the weight of the oral care composition.

Typically, at least 60 wt % or at least 80 wt % of the pumice, based on the weight of the pumice, has an average particle size of from 90 to 300 microns. Larger pumice particles outside of the desired range may impart unpleasant mouth feel when the oral composition is used and may be overly abrasive.

Typically, the second particulate abrasive comprises calcium carbonate in an amount of from 5 to 40 wt %, based on the weight of the oral care composition, for example from 15 to 30 wt %, based on the weight of the oral care composition.

Typically, the calcium carbonate has an average particle size of from 2 to 13 microns. In some embodiments, the calcium carbonate comprises natural calcium carbonate particles. Optionally, precipitated calcium carbonate may be used in place of or in addition to natural calcium carbonate. Typically, at least a portion of the particles of calcium carbonate comprise natural calcium carbonate which have an average particle size of no greater than a dentin tubule of a mammalian tooth. Typically, at least a portion of the particles of natural calcium carbonate have an average particle size of from 2 to 5 microns.

System for Relieving Dentin Hypersensitivity

As stated above, the system for relieving dentin hypersensitivity typically includes, in addition to the particles of calcium carbonate such as natural calcium carbonate as discussed above, a basic amino acid in free or salt form.

The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater.

Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine. In certain embodiments, the basic amino acid is arginine, for example, L-arginine, or a salt thereof, such as L-arginine bicarbonate.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium.

In various embodiments, the basic amino acid is present in an amount of 1 wt % to 20 wt % of the total composition weight, 5 wt % to 15 wt % of the total composition weight, for example about 10 wt % of the total composition weight.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity of a mammal, improving/maintaining systemic health, and/or occluding dentin tubules. The compositions typically have particular utility as prophy pastes.

Polymers and Adherent Materials

The oral compositions of the invention may optionally also include a polymeric adherent material to assist in the retention of the calcium carbonate particles within the dentin tubules under salivary flow and during exposure to acidic foods and beverages.

The polymeric adherent material may be any known or to be developed in the art that attaches to the surface of a mammalian tooth and/or to the heterogeneous biofilm which also may be present on a tooth's surface. Attachment may occur by any means, such as ionic interaction, van der Waal's forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), carboxymethyl cellulose (CMC).

The polymers may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises poly (methylvinylether/maleic anhydride). In another embodiment, a copolymer comprises poly (methylvinylether/maleic acid). In another embodiment, a copolymer comprises poly (methylvinylether/maleic acid) half esters. In another embodiment, a copolymer comprises poly (methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

Typically, the at least one polymer is present in an amount of from 0.1 to 5 wt % based on the weight of the oral care composition, more typically from 0.25 to 2 wt % based on the weight of the oral care composition.

Commercially-available polymers may be used in the present invention. It is understood that over time, the exact size, weight and/or composition of a commercially-available polymer may change. Based on the disclosure set forth herein, the skilled artisan will understand how to determine whether such polymers are useful in the invention.

Oral Care Compositions

The oral care composition may in particular be a dentifrice composition which may be a toothpaste, and optionally formulated as a prophy paste.

Optionally, the oral care composition may comprise a fluorine or fluoride compound which is a fluoride source to provide anti-cavity benefits. The fluoride source can be a source capable of providing free fluoride ions, including sodium fluoride, sodium monofluorophosphate, stannous fluoride, silver diamine fluoride, indium 10 fluoride, or zinc fluoride, or any combination thereof. Typically, the level of free fluoride ion is from 1100 to 1450 ppm F, suitable for over the counter use; or 5000 to 12, 300 ppm suitable for prescription or in-office use.

Alternatively the composition may be formulated as a "leave-on" composition which can be applied undiluted and left in the oral cavity for an extended period of time. Such a composition does not include any components or additives which would cause damage or irritation to the oral cavity.

The composition according to the invention may also comprise one or more further agents typically selected from an anti-plaque agent, a whitening agent, antibacterial agent, cleaning agent, a flavouring agent, a sweetening agent, adhesion agents, surfactants, foam modulators, abrasives, pH modifying agents, humectants, mouth feel agents, colorants, abrasives, tartar control (anticalculus) agents, saliva stimulating agents, nutrients and combinations thereof.

The oral care composition according to the present invention comprises an orally acceptable vehicle in a product such as a toothpaste or a gel. As used herein, an "orally acceptable vehicle" refers to a material or combination of materials that are safe for use in the compositions of the present invention, commensurate with a reasonable benefit/risk ratio.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

The oral care compositions described herein may be formulated into any delivery form that permits contact of the abrasive particles to the tooth surface. For example, the compositions may be formulated into a paste or a gel. The composition may contain any conventional excipients or binder for such compositions.

Excipients or binders can include, for example, humectants, colorants, flavorants, glycerin, sorbitol, xylitol, water or other solvents, gum bases, thickening agents, surfactants, carrageenan (rich moss), xanthan gum and sodium carboxymethyl cellulose, starch, polyvinyl pyrrolidone, hydroxyethyl propyl cellulose, hydroxybutyl methyl cellulose, hydroxypropyl methyl cellulose, and hydroxyethyl cellulose and amorphous silica. Typically, the excipient or binder is present in an amount of from 0.1 to 5 wt % based on the weight of the oral care composition, more typically from 0.25 to 2 wt % based on the weight of the oral care composition.

Optionally, the orally acceptable vehicle comprises glycerin as a humectant which is present in an amount of from 5 to 20 wt % based on the weight of the oral care composition, further optionally from 10 to 15 wt % based on the weight of the oral care composition.

Methods of Use

The oral care composition according to the present invention may be administered to or applied to a human or other animal subject. The composition is suitable for administration or application to the oral cavity of a human or animal subject.

The composition is applied to the teeth by any method set forth herein or known in the art.

In an embodiment, the pumice and calcium carbonate particle-containing composition, optionally further comprising an amino acid as a dentin tubule occluding agent, may be applied to the tooth via a prophy cup or via conventional brushing techniques (e.g., use of a toothbrush). In another embodiment, such a composition may be applied to the tooth via another method, such as manual application (e.g., applying a composition to a tooth using one or more fingers, rubbing onto the tooth surface, rubbing in a circular motion, etc. . . . ), or application using any known dental appliance or applicator. It will be understood, based on the disclosure set forth herein, that any method of applying a composition onto a tooth, optionally using varying degrees of physical pressure, is encompassed by the invention.

Desensitization of a tooth according to the invention may be measured by any technique set forth herein, or any technique known to the skilled artisan.

Application of the composition to the tooth surface preferably results in the introduction of the composition into one or more dentin tubules. The invention also includes within its scope several related methods. For example, the invention includes within its scope methods of reducing and methods of occluding a dentin tubule of a mammalian tooth, methods of protecting dentin from acid-mediated degradation, and methods of reducing dental sensitivity.

Each of these methods includes the steps of applying any of the compositions described above to the tooth surface. Application may be carried out by any method, so long as the dentin tubule occluding particles are placed in contact with the tooth surface. Application may be accomplished by brushing or prophylaxis such as by using a prophy cup.

Dental sensitivity may be reduced according to a method of the invention by applying a composition of the invention to a tooth surface. A composition may be applied using a traditional method, as described in detail elsewhere herein, or by any appliance or applicator, whether or not typically associated with dental use.

The prophylactic application may be at carried out at any known frequency employed by dental professionals for prophylactic cleaning, and may be carried out over a duration of time, e.g., up to one year, up to three years or for a lifetime.

Various embodiments now will be described with reference to the following non-limiting examples

EXAMPLES

Examples 1 to 7

Dentifrice compositions according to Examples 1 to 7 and having the respective formulae of Table 1 were prepared. The respective amounts of the various components are listed in Table 1. The specified pumice grades having respective particle sizes are well known in the art of manufacturing prophy pastes, and widely commercially available Each of these compositions were suitable for use as a prophylactic treatment for cleaning the teeth, by applying the composition formulated as a paste to the tooth surface when disposed in a prophy cup, a technique employed by dentists and other dental professionals.

Further, the compositions were formulated in order to provide relief against dental hypersensitivity. These compositions all included arginine bicarbonate and natural calcium carbonate which is known to provide efficacy against dental hypersensitivity. However, these compositions differed with regard to their abrasive systems.

In particular, in Examples 1 to 7 the composition comprised pumice having an average particle size of from 30 to 277 microns. Different pumice particle sizes were employed, as show in Table 1. Example 4 also included minor amount of a perlite abrasive.

The binder system of the compositions of Examples 1 to 7 provided an appropriate viscosity and rheology included xanthan gum.

TABLE 1

Prophy Pastes of Examples 1 to 7

| | Ex. 1 | Ex. 2 | Ex. 3 | Ex. 4 | Ex. 5 | Ex. 6 | Ex. 7 |
|---|---|---|---|---|---|---|---|
| Pumice (average particle size 30 μm, pumice grade FF) | | | | | | | 10.00 |
| Pumice (average particle size 95 μm, pumice grade O) | | | | | | | 21.00 |
| Pumice (average particle size 122 μm, pumice grade O ½) | 31.00 | | | | | | |
| Pumice (average particle size 188 μm, pumice grade O ¾) | | 31.00 | | 21.00 | 38.00 | 45.00 | |
| Pumice (average particle size 277 μm, pumice grade ½) | | | 31.00 | | | | |
| Perlite | | | | 10.00 | | | |
| Glycerin | 13.47 | 13.47 | 13.47 | 13.47 | 13.47 | 13.47 | 13.47 |
| CaCO3 (4.5 μm average particle size) | 15.00 | 15.00 | 15.00 | 15.00 | 15.00 | 8.00 | 15.00 |
| CaCO3 (9.5 μm average particle size) | 14.00 | 14.00 | 14.00 | 14.00 | 14.00 | 7.00 | 14.00 |
| L-arginine bicarbonate | 10.00 | 10.00 | 10.00 | 10.00 | 10.00 | 10.00 | 10.00 |
| Flavor | 1.10 | 1.10 | 1.10 | 1.10 | 1.10 | 1.10 | 1.10 |
| Sodium saccharin | 0.25 | 0.25 | 0.25 | 0.25 | 0.25 | 0.25 | 0.25 |
| Xanthan gum | 0.50 | 0.50 | 0.50 | 0.50 | 0.50 | 0.50 | 0.50 |
| Benzyl alcohol | 0.30 | 0.30 | 0.30 | 0.30 | 0.30 | 0.30 | 0.30 |
| Sodium fluoride or sodium monofluorophosphate | 0 to 9.32 | 0 to 9.32 | 0 to 9.32 | 0 to 9.32 | 0 to 9.32 | 0 to 9.32 | 0 to 9.32 |
| Titanium dioxide | 0.50 | 0.50 | 0.50 | 0.50 | 0.50 | 0.50 | 0.50 |
| Purified water | QS | QS | QS | QS | QS | QS | QS |

Since these compositions may be employed as prophy pastes in a prophylactic cleaning treatment, as is well known in the art it is important that the prophy pastes have a high pellicle cleaning ratio (PCR) and a low radioactive dentin abrasion (RDA). The overall efficacy may be expressed as a ratio between the pellicle cleaning ratio (PCR) and the radioactive dentin abrasion (RDA)—the higher the PCR/RDA ratio, the more effective is the prophy composition to achieve high tooth surface cleaning but with low abrasion of the tooth enamel surface.

PCR studies were conducted on the compositions of the Examples utilizing a standard PCR method, modified for prophy application. For these studies, stained bovine enamel specimens were used, stained using a combination of PGY broth, tea, coffee, mucin, $FeCl_3$, and *Micrococcus luteus*. A prophy device, capable of rotating at a 1500 rpm and 20 rpm platform speeds, was used to apply the prophy paste. A constant tension of 250 g was used to ensure that uniform force was used to apply each product. The prophy cup was filled with the appropriate paste and the specimens were prophied for 6 seconds.

RDA studies were conducted utilizing a standard RDA method, modified for prophy application. Radioactive bovine dentin specimens were used. The prophy treatment consisted of a 15-second prophy with slurry of the reference abrasive followed by a 15-second prophy with the appropriate prophy paste. The platform speed rotated the dentin specimen at 20 rpm and the cup speed was adjusted to 1800 rpm. The load (tension) on the specimens was 250 g.

The results for the PCR and RDA values for Examples 1 to 7 are summarized in Table 2.

TABLE 2

PCR and RDA values for Examples 1 to 7

| | PCR | RDA | PCR/RDA Ratio |
|---|---|---|---|
| Example 1 | 79 | 117 | 0.68 |
| Example 2 | 76 | 119 | 0.64 |
| Example 3 | 76 | 115 | 0.66 |
| Example 4 | 56 | 144 | 0.66 |
| Example 5 | 93 | 135 | 0.69 |
| Example 6 | 98 | 133 | 0.74 |
| Example 7 | 59 | 92 | 0.64 |

The PCA and RDA values for Examples 1 to 7 of Table 2 show that the PCR values are generally rather high, the RDA values are generally rather low, and importantly PCR to RDA ratio for the evaluated Examples are >0.6, preferably >0.64.

Comparative Examples 1 to 4

Dentifrice compositions according to Comparative Examples 1 to 4 and having the respective formulae of Table 3 were prepared. The respective amounts of the various components are listed in Table 3.

Comparative Example 1 is a negative control which contains a calcium carbonate and silica abrasive system, and no pumice abrasive. Comparative Example 2 is a positive control representing a conventional medium grit prophy paste which contains only pumice and no calcium carbonate in its abrasive system. Comparative Examples 3 and 4 are controls which include smaller particle size range pumice based abrasives in a calcium carbonate-containing abrasive system.

Each of these compositions were suitable for use as a prophylactic treatment for cleaning the teeth, by applying the composition formulated as a paste to the tooth surface when disposed in a prophy cup, a technique employed by dentists and other dental professionals.

In contrast to Examples 1 to 7, in Comparative Example 1 the composition comprised no pumice but instead comprised silica particles in combination with the calcium carbonate particles. In Comparative Example 2 the composition comprised pumice particles but no calcium carbonate particles. In Comparative Examples 3 and 4 the composition comprised pumice particles of smaller average particle size than in Examples 1 to 7, and in combination with the calcium carbonate particles.

The binder system of the compositions of Comparative Examples 1 to 4 provided an appropriate viscosity and rheology.

TABLE 3

Prophy Pastes of Comparative Examples 1 to 4

| | Comp. Example 1 | Comp. Example 2 | Comp. Example 3 | Comp. Example 4 |
|---|---|---|---|---|
| Pumice (average particle size 30 μm, pumice grade FF) | | | 21.00 | 15.50 |
| Pumice (average particle size 95 μm, pumice grade O) | | | 10.00 | 15.50 |
| Pumice (average particle size 188 μm, pumice grade O 3/4) | | 60.00 | | |
| Glycerin | 21.00 | 13.47 | 13.47 | 13.47 |
| CaCO3 (4.5 μm average particle size) | 15.00 | | 15.00 | 15.00 |
| CaCO3 (9.5 μm average particle size) | 14.00 | | 14.00 | 14.00 |
| L-arginine bicarbonate | 10.00 | 10.00 | 10.00 | 10.00 |
| Flavor | 1.00 | 1.10 | 1.10 | 1.10 |
| Sodium carboxymethyl cellulose | 0.50 | | | |
| Sodium saccharin | 0.25 | 0.25 | 0.25 | 0.25 |
| Colorant | 0.001 | | | |
| Silica (SYLODENT 756) | 31.00 | | | |
| Xanthan gum | | 0.50 | 0.50 | 0.50 |
| Benzyl alcohol | | 0.30 | 0.30 | 0.30 |
| Sodium fluoride or sodium monofluorophosphate | | 0 to 9.32 | 0 to 9.32 | 0 to 9.32 |
| Titanium dioxide | | 0.50 | 0.50 | 0.50 |
| Purified water | QS | QS | QS | QS |

PCR studies were conducted on the compositions of the Comparative Examples 1 to 4 utilizing a standard PCR method, modified for prophy application, in a similar manner as for the Examples described above. Again, RDA studies were conducted utilizing a standard RDA method, modified for prophy application, in a similar manner as for the Examples described above.

The results for the PCR and RDA values for Comparative Examples 1 to 4 are summarized in Table 4.

TABLE 4

PCR and RDA values for Comparative Examples 1 to 4

| | PCR | RDA | PCR/RDA Ratio |
|---|---|---|---|
| Comparative Example 1 | 46 | 140 | 0.33 |
| Comparative Example 2 | 97 | 246 | 0.39 |
| Comparative Example 3 | 59 | 111 | 0.53 |
| Comparative Example 4 | 53 | 92 | 0.58 |

The PCR and RDA values for Comparative Examples 1 to 4 of Table 4 show that even though individual PCR values may be low, individual RDA values can be high. Importantly, none of the compositions of the Comparative Examples has the PCR to RDA ratio >0.6, the minimum threshold achieved by the compositions of Examples 1 to 7.

Therefore, using the combination of pumice within the average particle size range required by the invention and calcium carbonate within the average particle size range required by the invention, the PCR/RDA ratio can be increased as compared to compositions not having this combination of abrasives.

The results of Tables 3 and 4 show that compared to the negative control of Comparative Example 1 there is a significant increase in the PCR by the addition of the pumice abrasive system to the calcium carbonate-containing abrasive system. However, by controlling the amount and particles size of the pumice abrasive added, the RDA value can be kept lower than the use of pumice alone, and the result is that a higher PCR/RDA ratio can be achieved, having a value greater than 0.6, as compared to the comparative compositions.

In order to assess the efficacy for dentin occlusion by the oral care compositions of Comparative Example 1 and Examples 2 and 6, hydraulic conductance experiments were conducted on these prophy pastes which all contained 8% L-arginine as well as natural calcium carbonate. This experiment was conducted using human dentin specimens with open dentin tubules. The paste was applied to each specimen using a standard prophy device, equipped with a rotary prophy cup.

The results from hydraulic conductance measurements are summarized in Table 5. These results show that the % flow reduction for the prophy pastes of Examples 2 and 6 incorporating pumice were equivalent or better than the non-pumice containing control of Comparative Example 1. This indicates that the incorporation of pumice into the formula does not negatively impact the occlusion benefit of desensitizing oral care compositions comprising active components for dentin tubule occlusion.

TABLE 5

Flow reduction

| | % Flow Reduction |
|---|---|
| Comparative Example 1 | 76% ± 8% |
| Example 2 | 92% ± 5% |
| Example 6 | 89% ± 8% |

In summary, the preferred embodiments of the invention can provide oral care compositions with not only an enhanced PCR/RDA ratio, representing high cleaning efficacy coupled with low dentin abrasion, but also high efficacy in dentin tubule occlusion to treat hypersensitivity.

The invention claimed is:

1. An oral care composition comprising an abrasive system, wherein the abrasive system comprises
   (a) a first particulate abrasive comprising 20-60 wt % pumice, based on the weight of the oral care composition, having an average particle size of from 20 to 300 microns; and
   (b) a second particulate abrasive comprising calcium carbonate having an average particle size of from 2 to 13 microns;
       wherein at least 80 wt % of the pumice, based on the weight of the pumice, has an average particle size of from 90 to 300 microns; and
       wherein the composition comprises from 21 to 45% by weight of pumice having an average particle size of 188 to 277 microns, and wherein the composition has a ratio of pellicle cleaning ratio (PCR) to radioactive dentin abrasion (RDA) from 0.64 to 0.8.

2. The oral care composition according to claim 1 wherein the composition comprises 38 to 45% by weight of 188 micron pumice.

3. The oral care composition according to claim 2 wherein the first particulate abrasive comprises from 30 to 50 wt % pumice, based on the weight of the oral care composition.

4. The oral care composition according to claim 1 wherein the second particulate abrasive comprises calcium carbonate in an amount of from 5 to 40 wt %, based on the weight of the oral care composition.

5. The oral care composition according to claim 4 wherein the second particulate abrasive comprises calcium carbonate in an amount of from 15 to 30 wt %, based on the weight of the oral care composition.

6. The oral care composition according to claim 1 wherein a weight ratio of the first particulate abrasive and the second particulate abrasive is within a range selected from the group consisting of 0.6-5.0:1, 0.7-4.0:1, and 1.0-3.5:1.

7. The oral care composition according to claim 1 wherein the calcium carbonate has an average particle size of from 4 to 10 microns.

8. The oral care composition according to claim 1 wherein the calcium carbonate comprises of a first calcium carbonate with an average particle size of from 4 to 5 microns and a second calcium carbonate with an average particle size of from 9 to 10 microns.

9. The oral care composition according to claim 8 wherein the weight ratio of the first calcium carbonate with an average particle size of from 4 to 5 microns to the second calcium carbonate with an average particle size of from 9 to 10 microns is selected from group consisting of 1.0-1.2:1 and 1.05-1.15:1.

10. The oral care composition according to claim 1 wherein the calcium carbonate comprises natural calcium carbonate particles.

11. The oral care composition according to claim 1 wherein at least a portion of the particles of calcium carbonate comprise natural calcium carbonate having an average particle size of no greater than a dentin tubule of a mammalian tooth.

12. The oral care composition according to claim 1 which further comprises a basic amino acid in free or salt form in an amount effective for treating dental hypersensitivity.

13. The oral care composition according to claim 12 wherein the basic amino acid in free or salt form comprises arginine bicarbonate.

14. The oral care composition according to claim 12 wherein the basic amino acid in free or salt form is present in an amount of from 5 to 15 wt % based on the weight of the oral care composition.

15. The oral care composition according to claim 14 wherein the basic amino acid in free or salt form is present in an amount of from 7 to 12 wt % based on the weight of the oral care composition.

16. The oral care composition according to claim 1 which further comprises an orally acceptable vehicle.

17. The oral care composition according to claim 16 wherein the orally acceptable vehicle comprises glycerin which is present in an amount of from 5 to 20 wt % based on the weight of the oral care composition.

18. The oral care composition according to claim 17 wherein the glycerin is present in an amount of from 10 to 15 wt % based on the weight of the oral care composition.

19. The oral care composition according to claim 1 further comprising a fluoride compound or a source of fluorine ions.

20. The oral care composition according to claim 1 wherein the amount and particle size of the first and second particulate abrasives are selected to provide the oral care composition with a pellicle cleaning ratio (PCR) of at least 59, and a radioactive dentin abrasion (RDA) of no more than 250.

21. The oral care composition according to claim 20 wherein the pellicle cleaning ratio (PCR) is from 70 to 110, and the radioactive dentin abrasion (RDA) is from 100 to 140.

22. The oral care composition according to claim 1 wherein the composition is formulated into a dentifrice in the form of a paste.

23. A method of cleaning teeth comprising applying the oral care composition of claim 1 to a tooth surface, the oral care composition being applied as a paste disposed in a prophy cup.

24. The oral care composition according to claim 1, wherein the calcium carbonate comprises a first calcium carbonate with an average particle size of from 4 to 5 microns and a second calcium carbonate with an average particle size of from 9 to 10 microns, in a weight ratio selected from group consisting of 1.0-1.2:1 and 1.05-1.15:1; and wherein the pellicle cleaning ratio (PCR) is from 70 to 110, the radioactive dentin abrasion (RDA) is from 100 to 140, and the PCR to RDA ratio is from 0.64 to 0.8.

* * * * *